(12) United States Patent
Ludoph

(10) Patent No.: US 10,413,201 B2
(45) Date of Patent: Sep. 17, 2019

(54) PRESSURE SENSOR CATHETER AND ASSOCIATED METHOD

(71) Applicant: Wellinq Medical B.V., Leek (NL)

(72) Inventor: Bas Ludoph, Leek (NL)

(73) Assignee: Wellinq Medical B.V., Leek (NL)

(*) Notice: Subject to any disclaimer, the term of this patent is extended or adjusted under 35 U.S.C. 154(b) by 476 days.

(21) Appl. No.: 14/419,726

(22) PCT Filed: Aug. 6, 2013

(86) PCT No.: PCT/NL2013/050582
§ 371 (c)(1),
(2) Date: Feb. 5, 2015

(87) PCT Pub. No.: WO2014/025255
PCT Pub. Date: Feb. 13, 2014

(65) Prior Publication Data
US 2015/0223707 A1    Aug. 13, 2015

(30) Foreign Application Priority Data

Aug. 6, 2012   (NL) .................................... 2009285
Dec. 7, 2012   (NL) .................................... 2009940

(51) Int. Cl.
*A61B 5/0215*    (2006.01)
*A61B 5/00*    (2006.01)
(Continued)

(52) U.S. Cl.
CPC ...... *A61B 5/02158* (2013.01); *A61B 5/02007* (2013.01); *A61B 5/0215* (2013.01);
(Continued)

(58) Field of Classification Search
USPC ........................................................ 600/487
See application file for complete search history.

(56) References Cited

U.S. PATENT DOCUMENTS 4,901,731 A * 2/1990 Millar .................. A61B 5/0215
600/486
5,573,007 A * 11/1996 Bobo, Sr. ............. A61B 5/0215
600/561
(Continued)

FOREIGN PATENT DOCUMENTS

JP    19940051396 A    9/1995
JP    19970190307 A    2/1999
(Continued)

*Primary Examiner* — Christian Jang
*Assistant Examiner* — Mitchell E Alter
(74) *Attorney, Agent, or Firm* — The Webb Law Firm

(57) ABSTRACT

The invention relates to a pressure sensor catheter and method for measuring pressure on a distal side of a flow constriction, such as a stenosis, in a body lumen or measuring a pressure difference over the flow constriction. The catheter includes a pressure transfer tube for passing through the constriction, the tube being connected to and extending from a pressure sensor for transferring the pressure at the distal side of the constriction via the tube to the sensor, and a catheter body for introduction of the catheter into the body lumen, wherein the catheter body comprises the sensor at a sensor position, such that the sensor in use is positioned in the body lumen, and wherein a distal end region of the catheter including the distal end region of the pressure transfer tube has a smaller maximum outer diameter than the outer diameter of the catheter at the sensor position.

19 Claims, 8 Drawing Sheets

(51) Int. Cl.
  *A61B 5/02* (2006.01)
  *A61M 25/00* (2006.01)
  *A61M 25/09* (2006.01)
  *A61M 25/01* (2006.01)

(52) U.S. Cl.
  CPC ......... *A61B 5/6852* (2013.01); *A61M 25/003* (2013.01); *A61M 25/005* (2013.01); *A61M 25/0009* (2013.01); *A61M 25/09* (2013.01); *A61B 2560/0257* (2013.01); *A61B 2562/0247* (2013.01); *A61B 2562/12* (2013.01); *A61M 2025/0003* (2013.01); *A61M 2025/0177* (2013.01); *A61M 2025/09125* (2013.01)

(56) References Cited

U.S. PATENT DOCUMENTS 6,019,728 A    2/2000  Iwata et al.
2003/0191400 A1   10/2003  Shalman et al.
2005/0187487 A1*  8/2005  Azizkhan ............. A61B 5/0215
                                                600/561
2007/0083126 A1*  4/2007  Marko ................ A61B 5/02007
                                                600/505
2011/0282217 A1* 11/2011  Nashef ............... A61B 5/02158
                                                600/488
2012/0299229 A1  11/2012  Kubo et al.
2013/0338637 A1* 12/2013  Fischer, Jr. ....... A61M 25/0026
                                                604/509

FOREIGN PATENT DOCUMENTS

JP    20030507111 A    6/2005
JP    2005348947    *  12/2005
JP    2005348947 A    12/2005
JP    20120501807 B2   1/2014
WO    8910089 A1    11/1989
WO    9956612 A1    11/1999

* cited by examiner

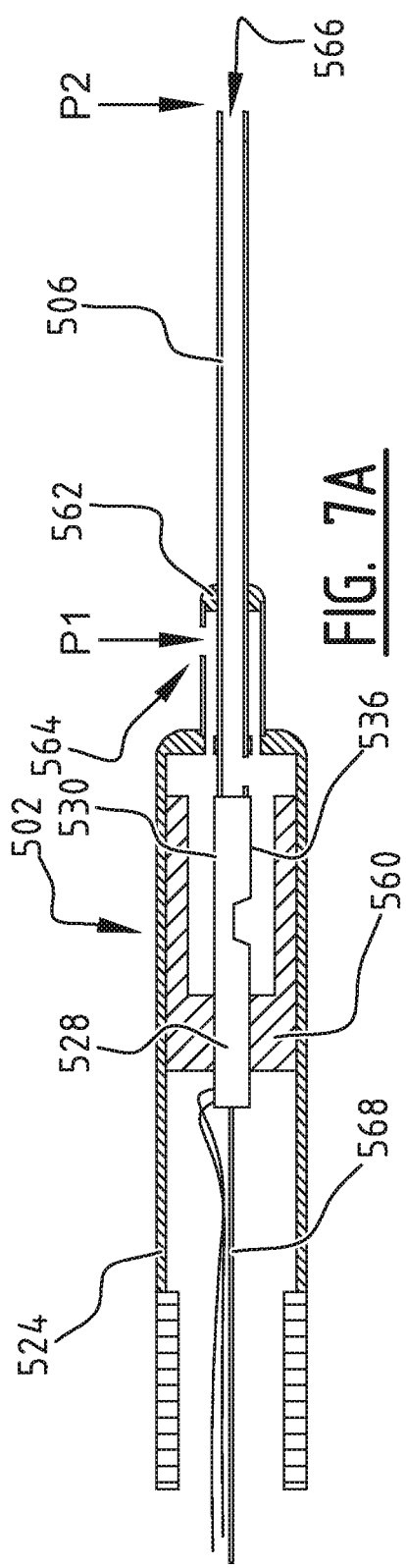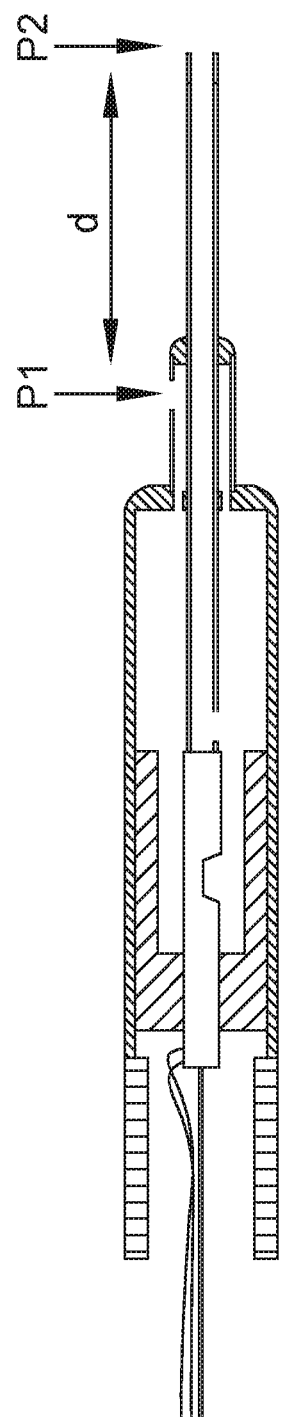
FIG. 7A
FIG. 7B

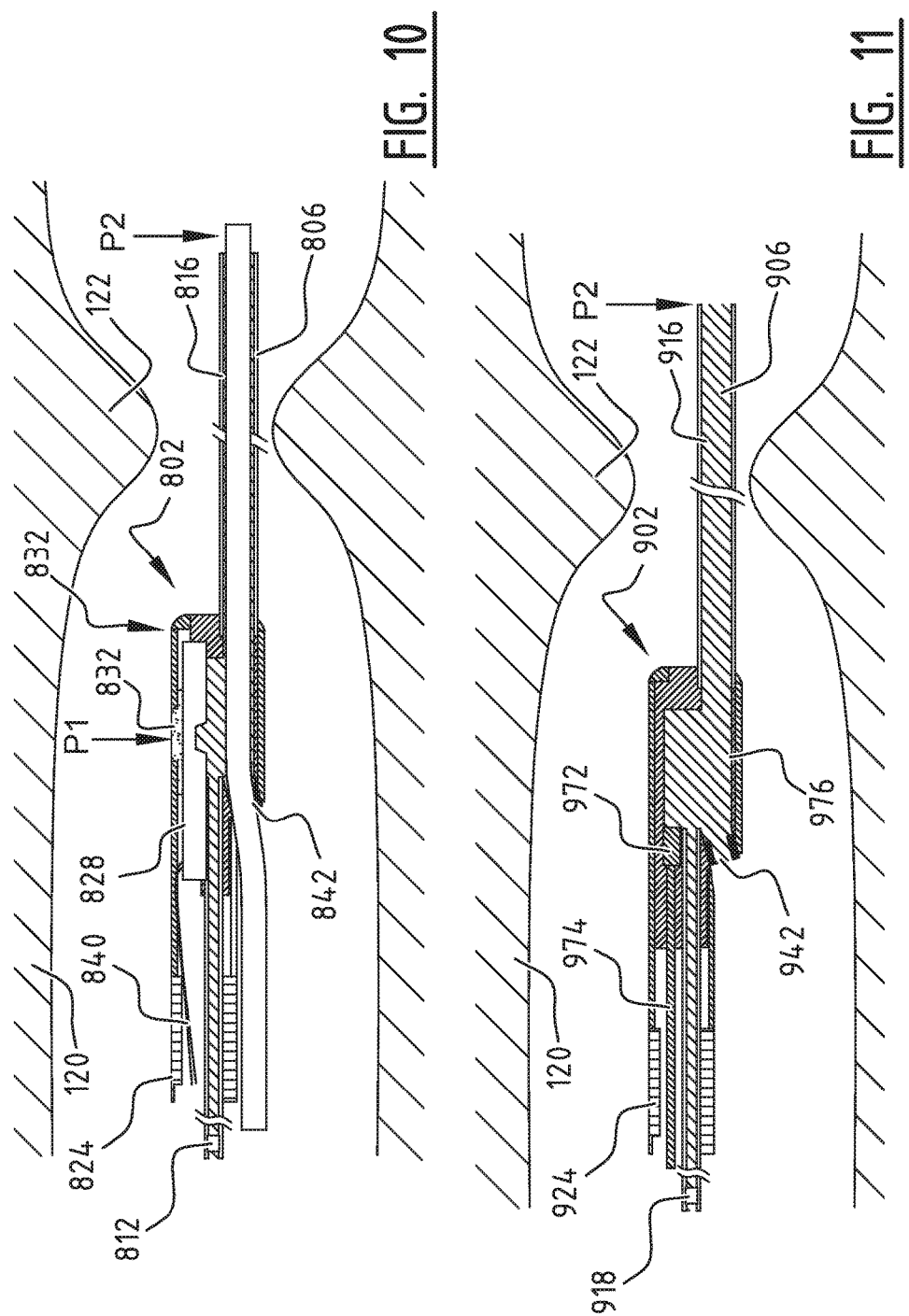

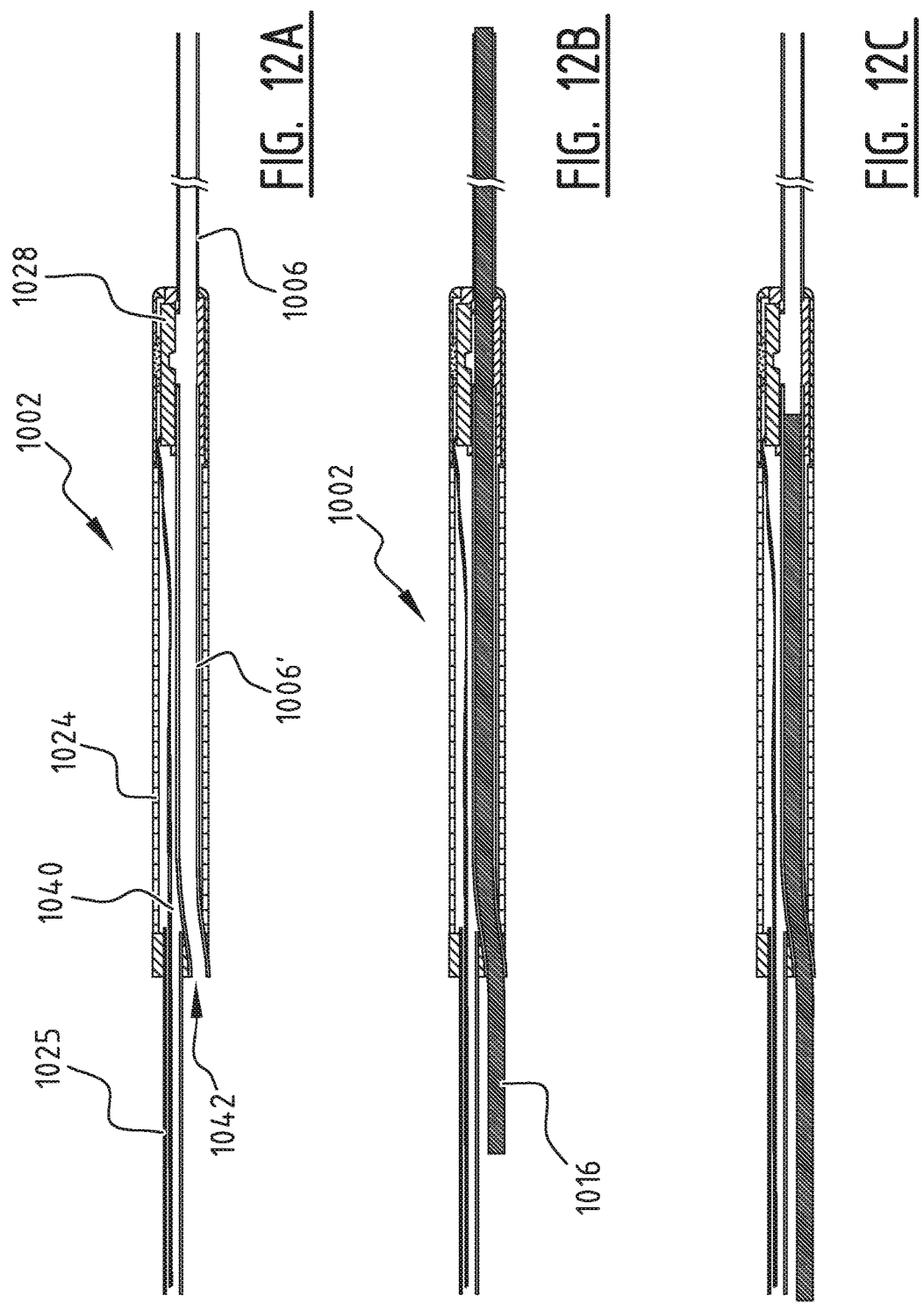

PRESSURE SENSOR CATHETER AND ASSOCIATED METHOD

CROSS-REFERENCE TO RELATED APPLICATIONS

This application is the United States national phase of International Application No. PCT/NL2013/050582 filed Aug. 6, 2013, and claims priority to The Netherlands Patent Application Nos. 2009285 and 2009940 filed Aug. 6, 2012 and Dec. 7, 2012, respectively, the disclosures of which are hereby incorporated in their entirety by reference.

BACKGROUND OF THE INVENTION

Field of the Invention

The invention relates to a pressure sensor catheter. This type of catheter is used for measuring pressures inside a body lumen.

Description of Related Art

These measurements can for example be used to calculate the fractional flow reserve (FFR). FFR provides a measure of the degree to which a stenosis obstructs the fluid flow in the body lumen, for example in a blood vessel. FFR is calculated on the basis of the pressure on the proximal side of the stenosis and the pressure on the distal side of the stenosis, typically at maximum vasodilation. For example, the pressures upstream and downstream of the stenosis are measured. The FFR ratio is defined as the downstream pressure divided by the upstream pressure. If the FFR ratio is low, a physician can decide to take appropriate actions, such as placing a stent. Typically, an FFR ratio below 0.75 is indicative of a stenosis which requires intervention.

In conventional pressure sensor catheters at least one pressure sensor has to be moved to the distal side of the stenosis to measure the pressure locally.

For example, in one type of conventional device, a sensor is mounted on the tip of a guidewire.

Moving the sensor through a stenosis requires a sensor which is as small as possible. Another reason for using a small sensor is to minimize the influence of the catheter on the blood flow and hence the measured pressure. To keep the sensor small in conventional devices, various compromises have been made in the design thereof. For example, the sensors are half-bridge sensors and/or do not comprise outside pressure equalization, both leading to less accurate measurements. In addition, mounting such a small sensor in a way that makes it insensitive to bending is complicated.

A goal of the invention is to overcome the above problems and to provide a pressure sensor catheter which can be introduced in a body lumen to accurately measure the pressure on the distal side of a flow restriction, such as a stenosis, even for narrow passages.

SUMMARY OF THE INVENTION

This goal is achieved with the pressure sensor catheter according to the invention for measuring a pressure on the distal side of a flow constriction in a body lumen, such as a stenosis, and/or for measuring a pressure difference between the pressure on a proximal side of the flow constriction and a pressure on the distal side of the flow constriction, the pressure sensor catheter comprising:
  a pressure sensor; and
  at least one pressure transfer tube for passing through the flow constriction, the tube being connected to and extending from the pressure sensor for transferring the pressure at the distal side of the flow constriction via the tube to the pressure sensor, comprising a catheter body for introduction of the pressure sensor catheter into the body lumen, wherein the catheter body comprises the sensor at a sensor position, such that the sensor in use is positioned in the body lumen, wherein a distal end region of the catheter comprising the distal end region of the pressure transfer tube has a smaller maximum outer diameter than the outer diameter of the catheter at the sensor position.

Preferably, the body lumen is a blood vessel.

The term 'catheter' is defined as a medical device for introduction in a body lumen, such as a blood vessel or urinary tract. Although other definitions may exist, in the context of the invention the aforementioned definition shall be applied. The term 'pressure sensor catheter' shall mean a catheter, i.e. a medical device for introduction in a body lumen, comprising a pressure sensor.

Although the invention will primarily be described with relation to measuring a pressure across or distal of a stenosis, the catheter according to the invention is further applicable to measure a pressure across or distal of a different narrowing or flow restriction in a body lumen, such as a heart valve.

By providing a pressure transfer tube, the part of the catheter that comprises the pressure sensor does not have to be guided past the flow constriction. The pressure transfer tube is guided to the distal side of the flow constriction instead. Therefore, the sensor dimensions are not limiting the applicability of the pressure sensor catheter.

Furthermore, since the pressure sensor and its wiring do not have to be maneuvered past the flow constriction, a bigger sensor or more wires may be used. For example, preferably the catheter comprises a full bridge sensor which has superior characteristics to a half bridge sensor and requires four connecting wires instead of three.

Furthermore, there is ample room on the proximal side of the flow constriction to provide the sensor with equalisation to ambient pressure, reducing drift and other unwanted effects.

In one embodiment the catheter comprises means arranged to provide ambient pressure equalization to the sensor. For example, one side of the sensor is connected to a lumen which in use is in fluid communication (i.e. gas or liquid communication) with ambient pressure, such that the sensor measures the pressure transferred via the tube relative to ambient pressure. Equalisation to ambient pressure is possible, however not required according to the invention.

In the context of the invention, distinction will be made between an absolute pressure measurement and a differential pressure measurement.

An absolute pressure measurement comprises measuring the pressure with respect to a substantially constant reference pressure. The reference may be ambient pressure, i.e. gauge pressure. A pressure sensor for measuring gauge pressure comprises ambient pressure equalization, e.g. one side of the sensor is in contact with ambient pressure. A sensor for measuring gauge pressure is referred to as gauge pressure sensor. Alternatively, the reference may be a constant pressure other than ambient pressure, i.e. the sensor has no ambient equalization. To this end, a pressure sensor may comprise a closed cavity such that the pressure is measured with respect to the pressure in the cavity. Such a sensor is referred to as a closed cavity sensor or sealed pressure sensor.

In the context of the invention a differential pressure measurement comprises measuring a pressure difference between the pressure at the distal side of the flow constriction and the pressure at the proximal side of the flow constriction. A sensor for measuring differential pressure is referred to as differential pressure sensor. Actually, a differential pressure sensor may be similar in construction to a gauge pressure sensor, however instead of using ambient pressure as a reference, one side of the sensor is exposed to the pressure at a distal side of the flow constriction and the other side of the sensor is exposed to the pressure at the proximal side of the flow constriction.

A further advantage of the invention is that a relatively small pressure transfer tube will have no or little influence on the fluid flow and, accordingly, on the pressure measurement.

The pressure sensor catheter can be introduced into the body lumen and positioned close to the flow constriction either through a guide catheter or over a guidewire or both. In particular in the case no guidewire is used to introduce the pressure sensor catheter into the body, it preferably comprises a soft atraumatic tip yet be firm enough to be passed through the guide catheter and cross a flow constriction. For example, the catheter comprises a flexible metal tube. If the pressure transfer tube is strong enough it may constitute the backbone of substantially the whole catheter, i.e. the catheter body and pressure transfer tube may be formed by a single flexible metal tube.

In the case a guidewire is used to introduce the pressure sensor catheter into the body, it for example comprises a seal at its proximal end allowing the guidewire to be fed through the full length of the pressure sensor catheter. Alternatively, the catheter comprises an opening in a side wall near the distal end of the pressure transfer tube and distal of the sensor for passing a guidewire through a distal region of the pressure transfer tube via the distal end opening of the tube and the side wall opening. In another alternative, the side opening is positioned proximal of the sensor.

According to the invention, various types of pressure sensors can be provided for measuring the pressure transferred via the pressure transfer tube. For example, an optical pressure sensor comprising an optical fibre can be provided. As another example, a piezo resistive or a piezo electric pressure sensor is provided. Furthermore, an absolute pressure sensor or a differential pressure sensor may be provided.

The distal end region of the catheter comprises the distal end region of the pressure transfer tube. This distal end region of the catheter has a smaller maximum outer diameter than the maximum outer diameter of the catheter at the sensor. In other words, the maximum outer diameter is substantially determined by the outer diameter of the pressure transfer tube, which can be made relatively small. For example, in case where the distal end region of the catheter is formed by the distal end region of the pressure transfer tube, its outer diameter is equal to that of the pressure transfer tube.

Therefore, the distal end region of the catheter can be made very small, i.e. preferably having a French size smaller than 2F (0.66 mm), more preferably smaller than 1.8 F (0.6 mm). More preferably smaller than 1.5 F (0.5 mm), even more preferably smaller than 1.2 F (0.4 mm) and most preferably smaller or equal to 1 F (0.33 mm), e.g. 0.8 F (0.266 mm) or 0.5 F (0.166 mm). The ideal size of the distal end region of the catheter will depend on, amongst other things, whether the pressure transfer tube in a certain embodiment will need to accommodate a guidewire. The catheter may have a part with an outer diameter larger than the outer diameter of the pressure transfer tube, e.g. such a part may house the pressure sensor. In that case, the distal part of the pressure transfer tube extends in the distal direction from said part, such that the distal part of the catheter comprises the distal part of the tube and has substantially the same outer diameter as the tube.

In some embodiments, the distal end of the catheter is formed by the distal end of the pressure transfer tube. In other embodiments, the tube may be provided with an atraumatic tip at its distal end. In such embodiments, the maximum outer diameter of the combination of tube and tip is smaller than the outer diameter of the catheter at the position of the sensor. In most cases, the tip will have an outer diameter substantially equal to or smaller than the pressure transfer tube.

The sensor catheter according to the invention comprises a catheter body for introduction of the catheter into the body lumen, wherein the catheter body comprises the sensor such that the sensor in use is positioned in the body lumen. In other words, the catheter body provides a housing for housing the pressure sensor.

In use, i.e. during measurement, the sensor is positioned on a proximal side of the stenosis, heart valve or other flow restriction, while the at least one pressure transfer tube is positioned on the distal side of the flow constriction.

By providing the sensor in the body lumen it is positioned close to the measurement location. In some types of conventional guiding catheters an absolute pressure sensor located outside of the patient's body measures the pressure at the distal end of the guiding catheter which will be on the proximal side of the flow constriction. However, due to the influence of gravity on the fluid in the guiding catheter, the measurement will be disturbed by movement of the guiding catheter relative to the external pressure sensor. The catheter according to the invention does not suffer from this problem, as the sensor is positioned inside the body lumen. Nevertheless, the catheter according to the invention may be used in combination with such a conventional guiding catheter, such that the catheter measures a pressure distal of the flow constriction with its sensor positioned inside the body lumen and the guiding catheter measures the pressure proximal of the constriction with a sensor positioned outside the body lumen. This may be advantageous in the case of an FFR measurement, wherein both the distal and proximal pressures are preferably measured, e.g. relative to ambient pressure. Instead of using the conventional guiding catheter for measuring the proximal pressure, the catheter may comprise a second sensor for measuring the proximal pressure. For example, the second sensor is provided with ambient pressure equalization, e.g. via a lumen. Also in that case, the second sensor is preferably positioned in the body lumen.

In a preferred embodiment of the catheter according to the invention the sensor is a differential pressure sensor comprising a first and second sensing area for measuring the pressure difference between the first and second sensing areas, wherein the at least one pressure transfer tube is connected to the first sensing area, such that the sensing areas are exposed to the pressure at different locations in the body lumen.

By using a differential pressure sensor the catheter according to the invention can measure the pressure difference over a flow constriction in a single measurement. In contrast, one type of conventional pressure sensor catheters provides two sensors and the pressure differences are calculated from the pressure readings from both sensors. This leads to inaccurate results as compared to the pressure sensor catheter according to the invention. Assuming that a measurement $S_1$ using sensor 1 has a standard deviation, i.e.

measurement error, of $\sigma_s$ and a measurement $S_2$ using sensor 2 has equal standard deviation, the standard deviation $\sigma_{diff}$ of the calculated difference diff=$|S_1-S_2|$ can be derived as $\sigma_{diff}=\sqrt{2}\sigma_s$. For a direct measurement of the difference with a single sensor, as in the invention, a measurement error $\sigma_t=\sigma_s$ applies. The direct measurement is therefore more accurate than the indirect calculation. Moreover, as the invention enables the use of more accurate sensors, with for instance larger size and/or full bridge design, in general $\sigma_t$ will be smaller than $\sigma_s$ and the measurement will be even more accurate.

In conventional pressure difference measurements the pressure measured by a pressure sensor located distally of a flow constriction is subtracted from a pressure proximal of the flow constriction measured by an external pressure sensor at the end of a guide catheter. Therefore, any movement of the distally located pressure sensor with regards to the distal end of the guide catheter will influence the measured pressure. The embodiment having a differential pressure sensor does not require such a measurement with a guiding catheter. Therefore, it does not suffer from the above problem. Also, in conventional pressure difference measurements the sensor positioned on the distal side of the flow constriction is a closed cavity sensor, which usually has a higher drift. As the above embodiment uses a differential pressure sensor, this problem is overcome, further improving measurement accuracy.

In other types of conventional catheters the pressure on one side of the flow constriction is measured first, then the catheter is repositioned and subsequently the pressure on the other side is measured. With the catheter according to the invention on the other hand, the pressure difference can be measured in a single measurement, without the need to displace the catheter between measurements.

For example, the pressure transfer tube of the catheter according to the invention is fed past the flow constriction and the second sensing area is in use located before the flow constriction, such that a pressure difference over the flow constriction is measured directly.

In a further preferred embodiment the pressure sensor catheter according to the invention comprises a second pressure transfer tube connected to the second sensing area of the sensor.

Two tubes are used to transfer the pressure of two different locations to the sensor. Since the pressure transfer tubes can be provided relatively small the influence of the tubes on the measurement can be minimized.

In a preferred embodiment according to the invention, the at least one pressure transfer tube is provided as a single tube having a first pressure transfer lumen and a second pressure transfer lumen.

This enables a very compact design of the pressure sensor catheter. The lumens of the single tube are provided with openings at different locations along the tube. Therefore, the first lumen transfers the pressure at a first location, being the location of the opening of the first lumen, to the pressure sensor, while the second lumen transfers the pressure at a second location being the location of the opening of the second lumen, to the sensor. Therefore, a pressure difference is measured between the two locations.

In a preferred embodiment the at least one pressure transfer tube is movable and/or adjustable in length.

By providing a tube which is movable and/or adjustable in length, the location from which the pressure is transferred by the tube can be varied. For example, the tube is movable and/or adjustable in length during use. In an alternative example, the tube is movable and/or adjustable in length and lockable. The distance between the locations where the pressures are measured is set, and subsequently the tube is locked in this position. Then the catheter is introduced in the body lumen.

In another example the tube is provided such that it can be cut to an appropriate length.

In a preferred embodiment, the pressure transfer tube comprises a flexible membrane. Preferably, the membrane seals the pressure transfer tube, which is preferably prefilled with a fluid. By providing the flexible membrane, such as a silicone membrane, the pressure at the flexible membrane is transferred via the tube to the sensor, without the fluid in the tube entering the body lumen and fluid from the body lumen entering the tube.

In a preferred embodiment according to the invention the at least one pressure transfer tube comprises a closing means for controlling fluid flow, such as a valve, plunger or piston.

Using the closing means the pressure transfer tube can be filled with a fluid for transferring the pressure via the tube. For example, an isotonic salt solution is provided. Before measuring, the closing means is closed, such that the tube transfers the pressure instead of displacing the fluid. Alternatively, the pressure transfer tube can be filled with blood or fluid from the body lumen. Preferably, when the fluid is blood, the tube comprises an anticoagulant.

In an example, the catheter comprises a second pressure sensor, e.g. an absolute pressure sensor.

In a further preferred embodiment the pressure sensor catheter according to the invention comprises a second pressure sensor for measuring pressure proximal of the flow constriction, e.g. an absolute pressure proximal of the flow constriction. Preferably, the catheter body comprises the second pressure sensor at a second sensor position, proximally of the first sensor, such that in use the second sensor measures the pressure proximal of the flow constriction.

This allows both the pressure difference over the flow constriction and the pressure proximal to the flow constriction to be measured accurately in one device.

Preferably, the second pressure sensor is provided in the catheter body.

In a preferred embodiment according to the invention the at least one pressure transfer tube has an outer diameter smaller than the width of the sensor.

This has the advantage that the tube can pass into regions of the body lumen for which the sensor is too large.

In a further preferred embodiment according to the invention the pressure transfer tube has a French size smaller than 2 F, preferably smaller than 1.8 F, more preferably smaller than 1.5 F, even more preferably smaller than 1.2 F and most preferably smaller or equal to 1 F. As 1 F corresponds to an external diameter of ⅓ mm, the above dimensions correspond to 0.66 mm, 0.6 mm, 0.5 mm, 0.4 mm and 0.33 mm. It is noted that typical dimensions of conventional pressure sensor catheters are in the order of 4 F to 8 F.

The pressure sensor catheter according to the invention can be introduced in a body lumen over a guidewire and/or in a guiding catheter. Alternatively the catheter is introduced without using a guidewire and/or guiding catheter. In the case no guidewire is used the distal end of the sensor catheter, for example the distal end of the pressure transfer tube, preferably comprises a soft tip, such as an atraumatic guidewire tip. Preferably, the pressure transfer tube in this case is provided from a material which is sufficiently stiff, such that the tube can pass a narrowing, but will not kink.

In a preferred embodiment according to the invention the at least one pressure transfer tube comprises an opening in its side wall for passing a guidewire through a distal region of the tube via the distal end of the tube and the side wall opening.

This has the advantage that a physician can use the guidewire that he is most experienced with. This enables an easy displacement of the pressure sensor catheter in the body lumen. Furthermore, only the distal region of the tube has to have dimensions to accommodate a guidewire, whereas the intermediate part between the distal region and the sensor can be provided with smaller diameter. The opening may for example be provided distal or proximal of the sensor. In a preferred embodiment the opening is provided at a distance from the pressure sensor on a proximal side of the pressure sensor.

In a further preferred embodiment, the catheter comprises a feedthrough opening connected to the pressure transfer tube for feeding a guidewire via the feedthrough opening through at least a part of the pressure transfer tube.

In one embodiment the feedthrough opening is provided with sealing means for sealing the opening when a guidewire has been fed through. Such a sealing means may comprise a flush port.

For example, the sealing means comprise a sealing ring, for example comprising silicone. When the guidewire is fed through the opening, the sealing means close any gaps between the guidewire and the opening.

Therefore, once the guidewire has been fed through the opening, the opening will not influence the pressure in the transfer tube. Would the sealing means be absent, then the pressure measurement would be disturbed, as the pressure transfer tube would be in fluid communication with the fluid outside the catheter via the opening. The feedthrough opening with sealing means is for example provided in the pressure transfer tube itself, or in a fluid chamber in the catheter body connected to the pressure transfer tube.

In a preferred embodiment, the feedthrough opening for the guidewire is provided at a distance from the pressure sensor on a proximal side of the pressure sensor.

In other words, the guidewire can be fed through the pressure transfer tube via the feedthrough opening of the pressure transfer tube which is located proximally to the sensor. Therefore, the guidewire is inserted and retracted via the opening proximally of the sensor.

This has the advantage that when the guidewire is positioned in the pressure transfer tube it extends through a substantial portion of the pressure transfer tube. Therefore, the requirements for a seal at the feedthrough opening are less stringent. In fact, if the inner diameter of the pressure transfer tube is chosen appropriately no seal may be required at all, especially in the case of a sufficiently large distance between the feedthrough opening and distal opening of the tube. For example, the distance between feedthrough opening and sensor is over 50 mm, preferably over 100 mm, more preferably over 150 mm, even more preferably over 200 mm and most preferably over 250 mm. The optimal exit point of the guidewire from the catheter will also be determined by the anatomy in which it is to be positioned, avoiding locations with sharp curves.

This embodiment may be used as follows. First a guidewire is inserted into the body lumen. Then the pressure sensor catheter is fed over the guidewire into the body lumen to the desired location. Subsequently the guidewire is retracted to a point proximal of the sensor, but remaining partly in the pressure transfer tube to form a seal. As the guidewire is no longer positioned in the distal part of the pressure transfer tube, a measurement can be taken subsequently.

Preferably, the pressure transfer tube has a narrow fit to a guidewire, i.e. the inner diameter of the tube is substantially equal to the outer diameter of the guidewire to further improve the seal, but preferably not so small as to induce significant friction.

In a preferred embodiment, the pressure transfer tube has a radiopaque tip for visualisation of the catheter using an imaging system when the catheter has been introduced into a body lumen. In a preferred embodiment the tube has a hydrophilic coating on its outer surface to make it easier to slide the tube past the flow constriction.

In a preferred embodiment, the pressure transfer tube is self-supporting.

As the distal end region of the pressure transfer tube is self-supporting, it does not require a guidewire for introduction or displacing in the body lumen. In other words, the catheter is guidewireless. Therefore, the catheter has a flexibility and strength that enables it to be introduced and displaced without a guidewire. This allows the inner diameter of the pressure transfer tube and the outer diameter of the catheter to be reduced to minimal dimensions.

In a preferred embodiment, the pressure transfer tube is formed by a tube comprising metal, such as steel. In one example, the tube has a guidewire-like structure. Guidewires are self-supporting and may have small diameters. A distinction from the structure of conventional guidewires is that the pressure transfer tube has to have an inner lumen, i.e. the guidewire-like structure has to be at least partially hollow.

Preferably, the catheter body and the pressure transfer tube are formed by the tube comprising metal, i.e. the guidewire-like structure. In other words, the catheter body and pressure transfer tube are formed by the metal tube. As the hollow guidewire-structure is self-supporting, no support structure for providing structural rigidity to the catheter body is required.

By providing the catheter body as a hollow guidewire, the catheter is easily maneuverable in the body lumen. Furthermore, the size of the catheter is reduced.

In a further preferred embodiment a housing for housing the pressure sensor is provided to the catheter body, wherein the housing is mechanically more stiff than the catheter body, i.e. the guidewire-like structure.

The guidewire-like structure of the pressure transfer tube and/or catheter body will in general be very flexible. However, the sensor may be damaged if the part to which it is attached makes a too sharp turn. Further, bending of the sensor will influence the pressure measurement. In the catheter of the invention, the housing for the sensor locally reduces the flexibility of the catheter body, thereby protecting the sensor from stresses and damage.

The metal tube may be provided with a coating, such as a hydrophilic coating.

The invention further relates to a method for measuring a pressure on a distal side of a flow constriction in a body lumen, such as a stenosis or heart valve, and/or a pressure difference between a pressure on a proximal side of the flow constriction and a pressure on the distal side of the flow constriction, comprising:

providing a pressure sensor catheter according to the invention as described above; and positioning the at least one pressure transfer tube into the body lumen such that the sensor is located proximal of the flow constriction and is exposed to the pressure on the distal side of the flow constriction via the pressure transfer tube.

Such a method provides the same effects and advantages as described above for the pressure sensor catheter according to the invention. Furthermore, the features of the catheter and method according to the invention can be combined as desired.

Preferably, the body lumen is a blood vessel. According to the invention, the method is in particular applicable to any narrowing in a blood vessel, such as a stenosis or heart valve.

In a preferred embodiment according to the method of the invention, the step of providing a pressure sensor comprises providing a differential pressure sensor for measuring the pressure difference between a first sensing area of the sensor and a second sensing area of the sensor, wherein the at least one pressure transfer tube is connected to the first sensing area, the method comprising positioning the at least one pressure transfer tube such that the first sensing area is exposed to the pressure on the distal side of the flow constriction and the second sensing area is exposed to the pressure on the proximal side of the flow constriction.

As described above in relation to the pressure sensor catheter according to the invention, this has the advantage that the pressure difference over the flow constriction is measured directly.

In a preferred embodiment the method according to the invention comprises providing a fluid in the at least one pressure transfer tube. For example, the fluid is provided by operating a valve in the pressure transfer tube. The fluid is for example an isotonic fluid or blood. The fluid may for example enter the pressure transfer tube by suction or pressure, for example using a piston or plunger.

Preferably, the method comprises the step of measuring the pressure at a distal side of the flow constriction and the pressure at a proximal side of the flow constriction. For example, the FFR ratio is calculated subsequently.

When both the pressure difference $P_{diff}$ over the flow constriction and the absolute pressure $P_{prox}$ at the proximal side of the flow constriction are measured, the FFR ratio and/or time integrals thereof can be calculated according to:

$$FFR_{ratio}(t) = 1 - \frac{P_{diff}(t)}{P_{prox}(t)}$$

The measurement errors $\sigma_{P_{diff}}$ and $\sigma_{P_{prox}}$ propagate as follows:

$$\sigma^2_{FFR_{ratio}} = \left(\frac{-1}{P_{prox}}\right)^2 \sigma^2_{P_{diff}} + \left(\frac{P_{diff}}{P^2_{prox}}\right)^2 \sigma^2_{P_{prox}} \quad (1)$$

For a conventional measurement of $P'_{prox}$ and $P'_{distal}$, the FFR ratio is calculated as $$FFR'_{ratio}(t) = 1 - \frac{P'_{distal}}{P'_{prox}},$$

and the measurement error is $$\sigma^2_{FFR'_{ratio}} = \left(\frac{-1}{P'_{prox}}\right)^2 \sigma^2_{P'_{distal}} + \left(\frac{P'_{distal}}{P'^2_{prox}}\right)^2 \sigma^2_{P'_{prox}} \quad (2)$$

As $P_{diff}$ will always be smaller than $P_{distal}$ expressed as an absolute pressure, the second term will be smaller for $\sigma^2_{FFR_{ratio}}$. Furthermore, as the invention allows the use of a more accurate sensor for measuring $P_{diff}$, in general $\sigma^2_{P_{diff}} < \sigma^2_{P_{distal}}$, such that the first term is smaller. Therefore, the resulting error will be smaller for the calculation according to the invention.

Moreover, expressing $\sigma^2_{FFR_{ratio}}$ and $\sigma^2_{FFR'_{ratio}}$ in terms of relative errors gives:

$$\sigma^2_{FFR_{ratio}} = (1 - FFR_{ratio})^2 \left[\frac{\sigma^2_{P_{diff}}}{P^2_{diff}} + \frac{\sigma^2_{P_{distal}}}{P^2_{distal}}\right]$$

Assuming that the relative errors at the right hand side are approximately equal, it follows that $$\frac{\sigma_{FFR_{ratio}}}{\sigma_{FFR'_{ratio}}} \approx \frac{1 - FFR_{ratio}}{FFR'_{ratio}}$$

In the most relevant measurement range, with FFR ratio ≈0.75, the error of the method according to the invention is approximately 3 times smaller than in conventional methods. It is noted that the relative error $$\frac{\sigma^2_{P_{diff}}}{P^2_{diff}}$$

will in general be smaller due to the use of a better sensor. Therefore, the accuracy of the method of the invention will be even higher.

In a preferred embodiment, the method is practiced with a catheter wherein the pressure transfer tube comprises a feedthrough opening for feeding a guidewire via the feedthrough opening through at least a part of the pressure transfer tube, wherein the feedthrough opening is provided at a distance from and proximal of the pressure sensor. With such a catheter, the method preferably comprises the step of inserting the catheter over a guidewire positioned in the pressure transfer tube and the step of withdrawing the guidewire to a position in the pressure transfer tube proximal of the pressure sensor to form a pressure seal.

As explained above with respect to the catheter according to the invention, in this position the guidewire extends from the feedthrough opening to a point proximally of the sensor. Therefore, no guide wire is present in the part of the tube connecting the sensor to the measuring opening of the tube. This allows a correct measurement. At the same time, at the proximal side of the sensor a pressure seal is formed by the presence of the guidewire in the tube, improving the quality of the measurement.

BRIEF DESCRIPTION OF THE DRAWINGS

Further advantages, features and details of the invention will be elucidated on the basis of the preferred embodiments thereof, wherein reference is made to the accompanying drawings, in which:

FIG. 7A-B show an alternative embodiment, wherein the pressure transfer tube can be displaced;

FIG. 10 shows a so called rapid exchange version of a catheter according to the invention, wherein the catheter is provided with a feedthrough opening;

FIG. 11 shows an alternative embodiment of the rapid exchange catheter of FIG. 10, wherein an optical pressure sensor is used; and FIG. 12A-12C show a third embodiment of a rapid exchange catheter according to the invention, wherein the guidewire is inserted proximally to the sensor.

DETAILED DESCRIPTION OF THE INVENTION

Figure 1:
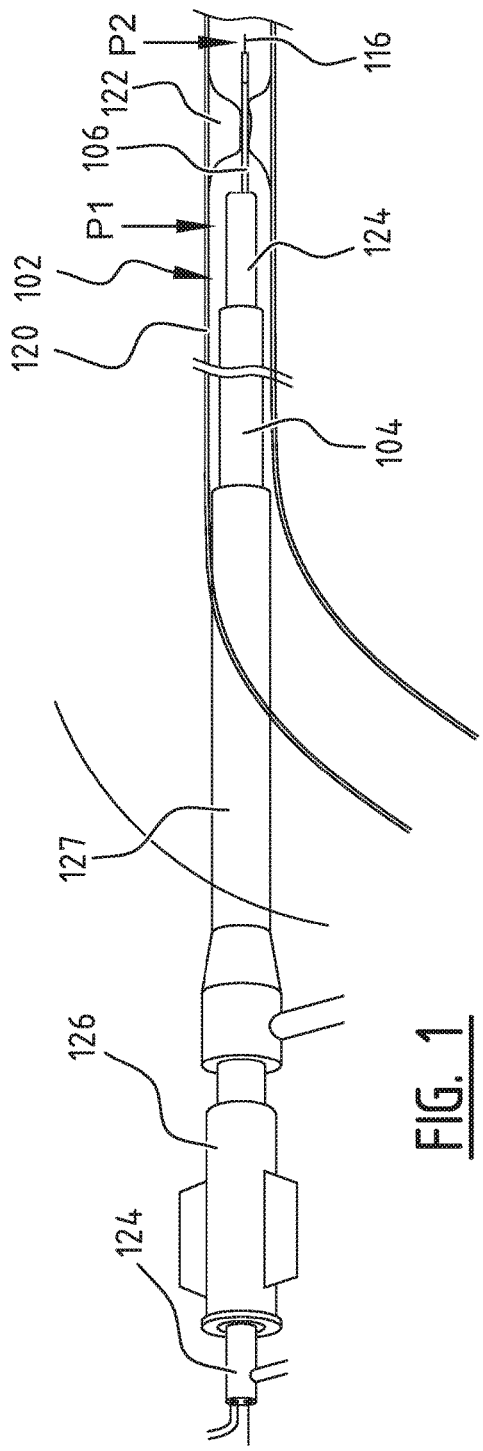
FIG. 1 shows a first embodiment of a pressure sensor catheter according to the invention.

Catheter 102 (FIG. 1) is positioned in a blood vessel 120. The pressure transfer tube 106 is guided over a guidewire 116. The tip of the pressure transfer tube is positioned at a distal side of a stenosis 122 in blood vessel 120. The tip of tube 106 forms the distal end of catheter 102. The sensor is provided in a catheter body 124. The catheter body 124 is provided through guiding catheter 104. Outside the body a hub 126 for manipulation of guiding catheter 104 is provided. Further, a sheath 127 is provided. The pressure transfer tube 106 extends beyond the catheter body 124.

Figure 2:
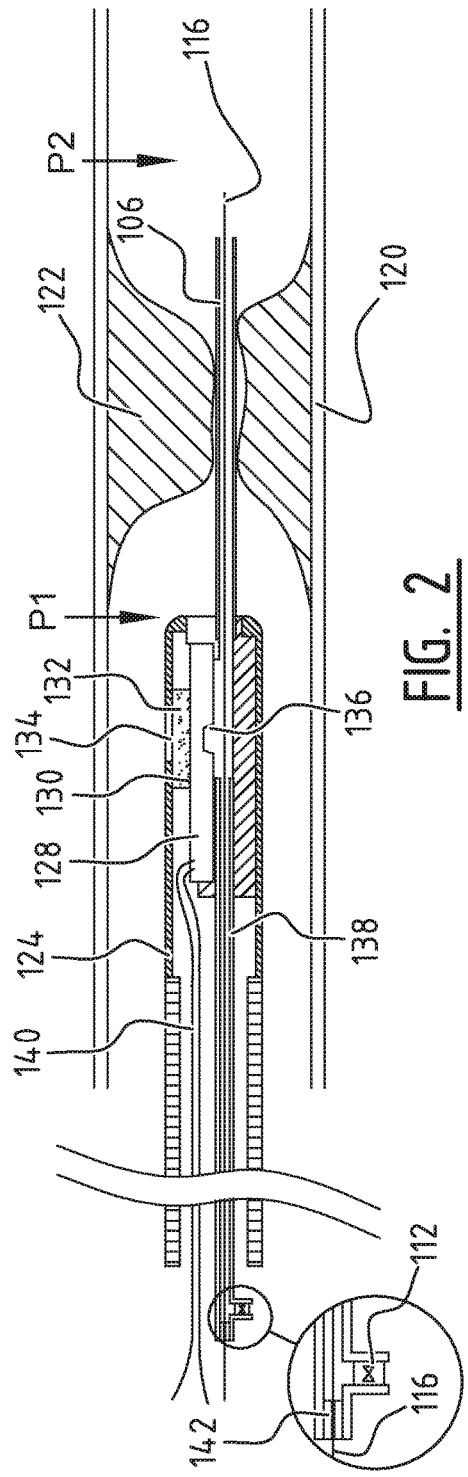
FIG. 2 shows the catheter of FIG. 2 in more detail.

The catheter body 124 holds a pressure sensor 128 (FIG. 2). In particular, the pressure sensor 128 is positioned within the catheter body 124. One side 130 of sensor 128 is exposed to a first pressure $P_1$ possibly via a silicone membrane or other flexible membrane 132 which is placed in front of an opening 134 in catheter body 124. The other side 136 of sensor 128 is exposed to pressure $P_2$ which is transferred via pressure transfer tube 106 to the catheter body 124. The pressure transfer tube 106 is filled with a fluid. The pressure transfer tube 106 continues through catheter body 124 towards the proximal side of the catheter by means of tube section 138. However, the pressure transfer tube 106 extends into the catheter body 124 along only a partial length of the catheter body 124. The sensor 128 is connected to wires 140. It is noted that the guidewire 116 is optional. A feed through 142 is provided for the guidewire. With valve 112 the fluid, such as a liquid, can be provided in pressure transfer tube 106.

Figure 3:
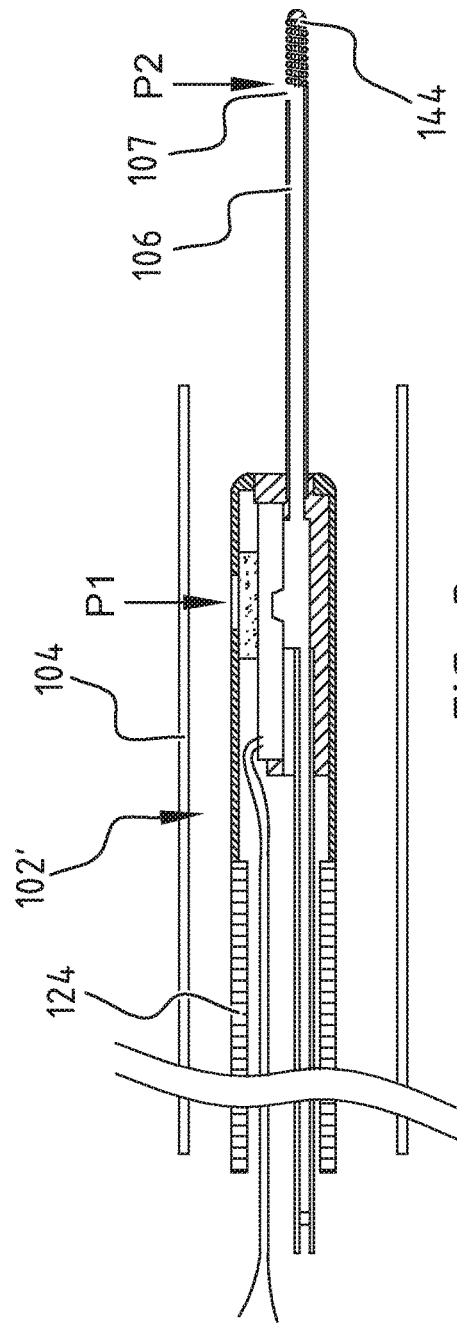
FIG. 3 shows a second embodiment according to the invention.

Sensor catheter 102' (FIG. 3) does not require a guidewire. Catheter 102' is fed into the body lumen using a guiding catheter 104. The pressure transfer tube 106 requires sufficient strength and flexibility to cross a stenosis and may comprises a tube having a guidewire-like structure. The tip 144 of the tube 106 is an atraumatic tip as known from conventional guidewires. Alternatively, a different soft tube end can be provided to tube 6, such as a soft tube section.

In an alternative embodiment of the sensor catheter 202 (FIG. 4), the pressure transfer tube 206 comprises a side opening 246. The guidewire 216 can be fed through the distal opening 248 and the side opening 246 of the pressure transfer tube 106.

Figure 5:
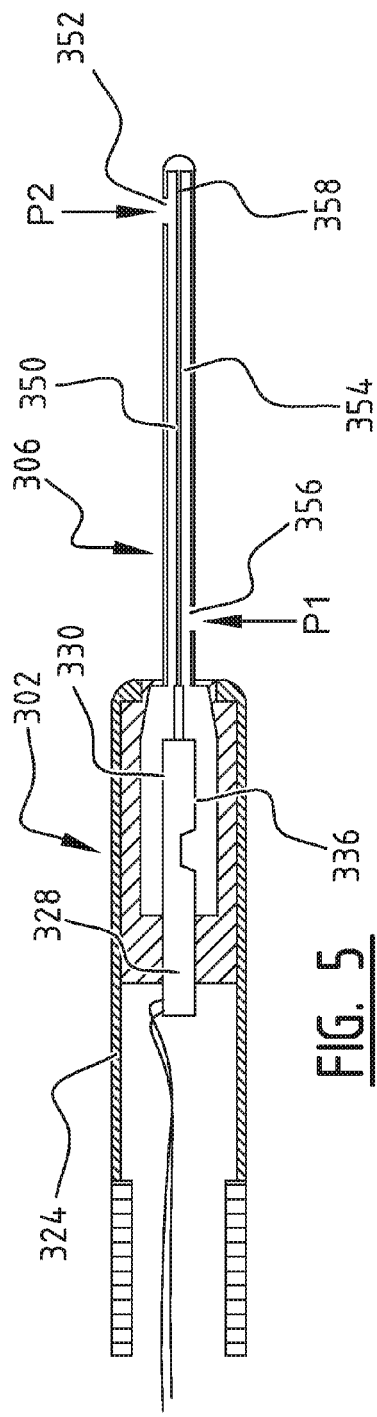
FIG. 5 shows a fourth embodiment according to the invention, comprising a double lumen.

Sensor catheter 302 (FIG. 5) comprises a pressure transfer tube 306 with a double lumen. The first lumen 350 comprises an opening 352 for transferring pressure $P_2$ to the upper side 330 of sensor 328. The second lumen 354 comprises an opening 356 for transferring pressure $P_1$ to sensing area 336 of sensor 328. The lumens 350, 354 are separated from each other by internal wall 358.

Figure 6:
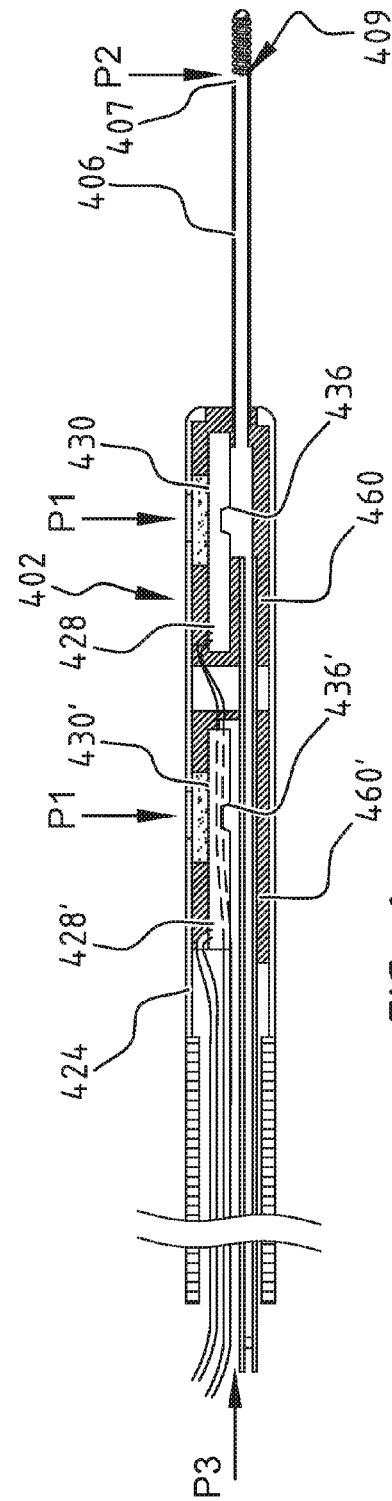
FIG. 6 shows a fifth embodiment according to the invention, comprising a second sensor for measurement of an absolute pressure on the proximal side of a flow constriction.

Sensor catheter 402 (FIG. 6) comprises a sensor tube 406 provided with an opening 407 and a soft tip 409. Catheter body 424 comprises two sensors 428, 428'. The sensor 428 at the distal end of catheter body 424 has a first side 430 which is exposed to pressure $P_1$ via flexible membrane 432. The other side 436 of sensor 428 is in contact with the fluid in tube 406, such that it experiences pressure $P_2$.

Sensor 428' has a first sensing side 430' exposed to pressure $P_1$ via flexible membrane 432'. The other side 436' of sensor 428' is connected to ambient pressure $P_3$.

Figure 4:
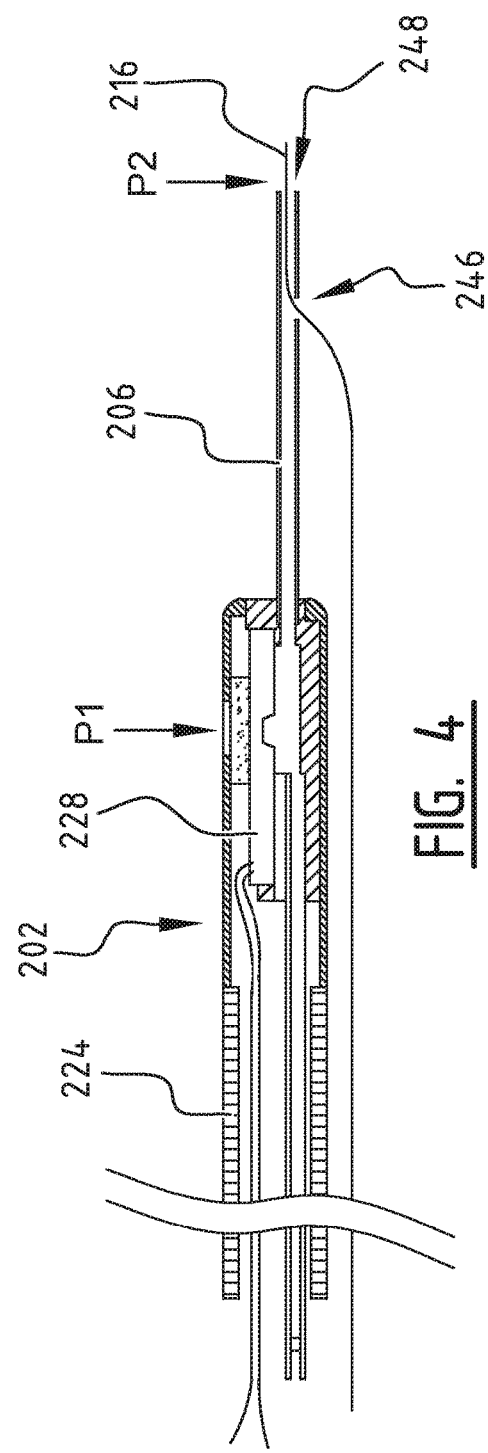
FIG. 4 shows a third embodiment according to the invention.

For example, tube 406 may be a hollow guidewire structure, e.g. a hollow metal tube, but may also comprise a tube through which a conventional guidewire is passed at least over some distance (as is shown in FIGS. 2 and 4). Sensor catheter 502 (FIG. 7A-B) is provided with a catheter body 524 which comprises sensor module 560. The sensor 528 is attached to sensor module 560. The catheter body 524 comprises a tip region 562 with an opening 564 for transferring pressure $P_1$ to a first sensing side 530 of sensor 528. Pressure $P_2$ is transferred via pressure transfer tube 506 to the second sensing side 536 of sensor 528.

Figure 8:
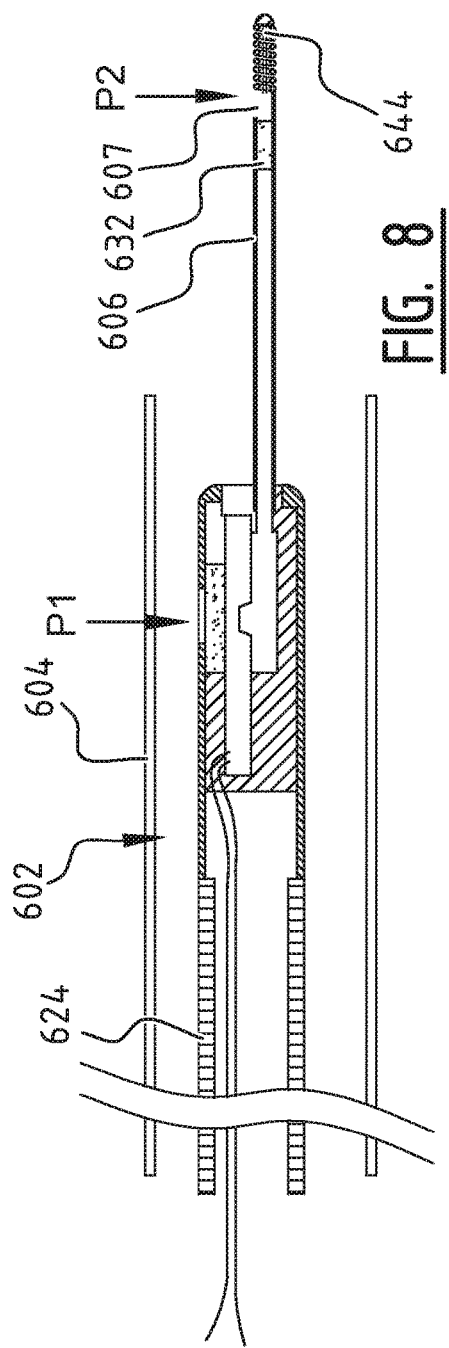
FIG. 8 shows an alternative embodiment comprising a pressure transfer tube with a membrane.

The sensor module 560 can be displaced inside catheter body 524 to vary the distance d between opening 564 and opening 566, as shown in FIGS. 8A and 8B. For example, the sensor module 560 is displaced before the catheter enters the body lumen. For example, the sensor catheter comprises means for locking the tube in its position relative to the other measurement location. Optionally, the sensor catheter is provided with means 568 to displace the sensor module while the catheter 502 is inside the body lumen.

Sensor catheter 602 (FIG. 8) comprises a tube 606 which is provided with a flexible membrane 632 to transfer the pressure at the tubes distal end via the tube 6 towards the sensor. The tube 606 is prefilled with fluid, preferably a liquid such as an isotonic salt solution.

Figure 9:
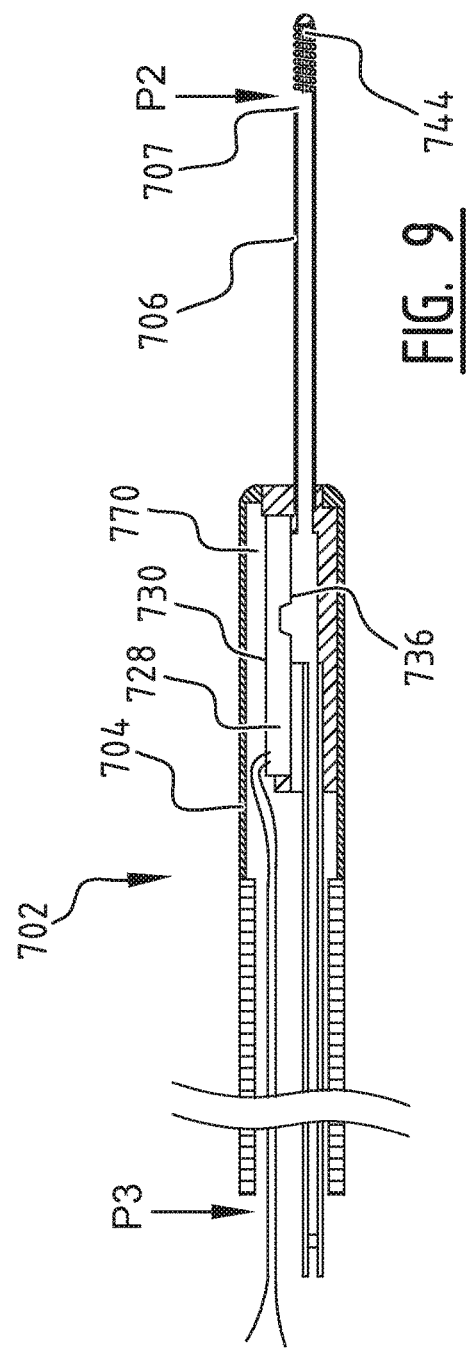
FIG. 9 shows a further embodiment of a catheter according to the invention, in which the sensor measures the pressure relative to ambient pressure.

Sensor catheter 702 (FIG. 9) comprises catheter body 704. Pressure transfer tube 706 is provided to transfer the pressure $P_2$ at opening 707 at the distal end to the lower side 736 of sensor 728. The upper side 730 of the sensor 728 is exposed to ambient pressure $P_3$ via the inside 770 of the catheter body.

Sensor catheter 702 can be used to measure the pressure difference between a distal side and a proximal side of a stenosis or heart valve by first positioning the catheter 702 such that the opening 707 of tube 706 is positioned at the distal side of the stenosis or heart valve and then repositioning the catheter 702 such that the tube 706 measures the pressure at the proximal side. Of course, one can alternatively measure the pressure at the proximal side first and the pressure at the distal side subsequently or measure the proximal pressure using a guiding catheter connected to a pressure sensor.

Sensor catheter 802 (FIG. 10) is provided in blood vessel 120 having stenosis 122. Catheter 802 comprises pressure transfer tube 806. The distal end of tube 806 has an opening which is exposed to pressure $P_2$ at the distal side of stenosis 122. This pressure is transferred via tube 806 to one side of full bridge pressure sensor 828. The other side of sensor 828 is exposed to pressure $P_1$ at the proximal side of stenosis 122, via flexible silicon membrane 832. Sensor 828 is connected to wires 840 for output of its electrical signals.

Catheter 802 further comprises a catheter body 824. The body has an inner fluid chamber connected with tube 806. This chamber is provided with a feed through opening 842. Feedthrough opening 842 comprises silicone elements, or other sealing elements. A 0.014 inch guidewire 816 is fed through the feedthrough opening 842 and pressure transfer tube 806. The silicone elements of opening 842 seal any gaps between the guidewire 816 and opening 842.

The outer diameter of catheter body 824 is French 4 (1.33 mm). The outer diameter of tube 806 is about French 1.5 (about 0.5 mm). The inner diameter of tube 806 is about 0.4 mm.

Catheter 902 (FIG. 11) is similar to catheter 802 of FIG. 10. It differs in that it is provided with an optical pressure sensor 972. The optical pressure sensor is connected to an optical fibre of outputting its optical signal for determining the pressure. It is noted that catheter 902 performs a measurement of $P_2$ alone. A second optical sensor can be provided to measure $P_1$ additionally. As in FIG. 10, feed through opening 942 is provided with a silicone sealing element. When a guidewire has been fed via this opening 942, through pressure transfer chamber 976 and pressure transfer tube 906, the sealing element seals any gaps between the guidewire and opening 942.

Catheter 1002 (FIG. 12A-12C) has a pressure transfer tube 1006 which extends distally from a catheter body 1024. For example, the tube 1006 extends 50-300 mm beyond the sensor. On the proximal side of sensor 1028 the pressure transfer tube continues as part 1006'. The catheter body 1024 houses the sensor 1028. The lower side of sensor 1028 is exposed to the liquid in tube 1006. The pressure transfer tube 1006 has a feed through opening 1042 located at a distance of 150-250 mm from sensor 1028. A guidewire 1016 can be fed through the tube 1006, 1006' (FIG. 12B), for insertion of catheter 1002 into the body lumen. The wires 1040 for transporting the signals from sensor 1028 are fed through an auxiliary tube 1025. This can be a (balloon) hypertube. Tube 1025 is for example 500-1200 mm in length.

During measurement the guidewire 1016 is withdrawn to a position proximal of the sensor (FIG. 12C). The guidewire is not completely withdrawn from the tube 1006, 1006' and therefore is positioned in the tube from the feed through opening 1042 to approximately the sensor 1028. Thereby, the guidewire 1016 effectively seals the opening 1042. Therefore, no separate seal has to be provided.

Tube 1006, 1006' has an outer diameter of 0.45 mm and an inner diameter of 0.38 mm. Housing 1024 has an outer diameter of 1.25 mm.

Figure 13:
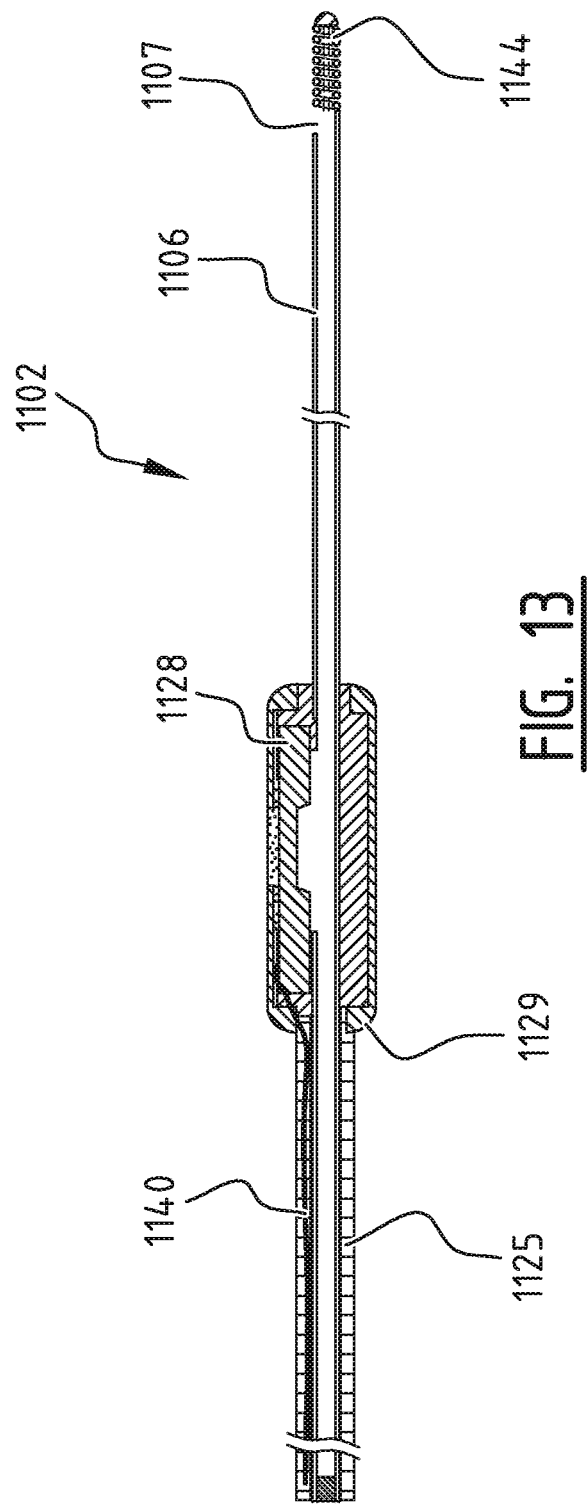
FIG. 13 shows an embodiment of a catheter according to the invention comprising a hollow guidewire-like structure.

Catheter 1102 (FIG. 13) comprises a pressure transfer tube 1106 which is provided as a hollow guidewire-like structure, in this case a hollow metal tube. Although the catheter 1102 will not be used for the function of a guidewire, i.e. it will not be used to guide a catheter, it has a similar structure as conventional guidewires. Tube 1106 has a side opening 1107 at a distal end region. The distal tip of the tube 1106 is provided with a guidewire tip 1144 of 20-50 mm length. The catheter 1102 comprises a Luer connector (not shown) at its proximal end for flushing the tube and for closing the tube. A sensor 1128 has its lower side in contact with the hollow space inside the tube 1106. The sensor 1128 is provided in a sensor housing 1129. The sensor housing is attached to the metal tube forming the catheter body and pressure transfer tube. It provides mechanic stability to the catheter body at the location of the sensor. This prevents damaging of the sensor and influencing pressure measurement in case the guidewire 1106 makes a (sharp) bend. The sensor 1128 is connected with wires 1140, which are provided at the outside of the hollow guidewire 1106. In this embodiment, wires 1140 are provided in an optional wiring encapsulation 1125. Encapsulation 1125 is provided on the hollow guidewire 1106. Alternatively, the wires 1140 can for example be fed through the lumen of the catheter or be attached to or integrated in the walls of the catheter.

The outer diameter of tube 1106 is 0.38 mm. The inner diameter is 0.15 mm. The housing 1129 has an outer diameter of 0.7 mm. On the distal side of sensor 1128 tube 1106 extends over a length of 50-300 mm. On the proximal side of sensor 1128 the catheter has a length of 500-1200 mm.

It is noted that an optical sensor 972 can also be used in other embodiments, instead of or in addition to sensors 128, 228, 328, 428, 428', 528, 728, 828, 1028, 1128.

An example of the method according to the invention will be illustrated by reference to FIG. 4. It is noted that the method can also be applied using the other embodiments of the catheter as described above.

To measure a pressure difference between a pressure on a proximal side of a stenosis or a heart valve and a pressure on a distal side of the stenosis or heart valve, first a guidewire 216 is introduced into the body lumen and past the stenosis. Subsequently, the proximal end of the guidewire is fed through tube 206 via openings 246, 248. The sensor catheter is then introduced inside the body lumen by advancing the sensor catheter 202. Once the opening 246 has passed the stenosis or heart valve, a measurement is recorded. At that moment the pressure P2 is equal to the pressure on the distal side of the stenosis or heart valve and the pressure P1 is the pressure on the proximal side of the stenosis or the heart valve. Therefore, the measurement by sensor 228 provides the pressure difference between $P_1$ and $P_2$, i.e. the pressure drop over the stenosis or heart valve. This is used to calculate the FFR. In case the FFR is below a critical value, such as 0.75, a physician can decide to take appropriate actions. The method may further comprise feeding a guiding catheter into the body lumen prior to feeding the sensor catheter 202 into the body lumen. Furthermore, the guiding catheter may comprise a pressure sensor or the sensor catheter 202 may comprise an additional pressure sensor to provide an absolute measurement of the pressure P1.

In the embodiment of FIGS. 5, 7A-7B and 8, the pressure transfer tube is in fluid communication with a closed inner volume in the catheter body. In contrast, in the embodiments of FIGS. 1-4, the tube continues beyond the sensor, for feeding a fluid from outside the body in the tube. Alternatively, the embodiments of FIGS. 5, 6, 7A-7B and 8 may comprise a tube for providing a fluid externally and the embodiments of FIGS. 1-4 may comprise a closed inner volume. For example, in the embodiment of FIG. 12 the fluid may be pre-filled before the procedure using a syringe. Embodiments are envisioned that are prefilled with fluid and have a flexible membrane sealing the respective pressure transfer tube opening.

The aforementioned exemplary embodiments according to the invention cover three types of catheters:
- an "over-the-wire" type (FIGS. 1 and 2) in which the catheter is guided over a guidewire extending through substantially the entire catheter;
- a "rapid exchange" type (FIGS. 4, 10-12) in which the guidewire passes through a side opening such that the guidewire extends through only a part of the catheter, wherein the opening may be located proximal of the sensor (FIG. 12), near the sensor (FIGS. 10, 11) or distal of the sensor (FIG. 4) and a "guidewireless" type (FIGS. 3, 5-9 and 13) in which the catheter is not required to be fed over a guide wire.

The present invention is by no means limited to the above described preferred embodiments thereof. The rights sought are defined by the following claims, within the scope of which many modifications can be envisaged. For example, it is explicitly mentioned that the combinations of the illustrated embodiments are possible.

The invention claimed is:

1. A pressure sensor catheter for measuring a pressure on a distal side of a flow constriction in a body lumen and/or for measuring a pressure difference between a pressure on a proximal side of the flow constriction and a pressure on the distal side of the flow constriction, comprising:
   a pressure sensor; and
   one pressure transfer tube for passing through the flow constriction, the pressure transfer tube being connected to and extending from the pressure sensor for transferring the pressure at the distal side of the flow constriction via the pressure transfer tube to the pressure sensor, the catheter comprising a catheter body for introduction of the pressure sensor catheter into the body lumen, wherein the catheter body has the sensor at a sensor position within the catheter body, such that the sensor in use is positioned in the body lumen, and wherein a distal end region of the catheter comprising the distal end region of the pressure transfer tube has a smaller maximum outer diameter than the outer diameter of the catheter at the sensor position, and wherein the pressure transfer tube extends beyond the catheter body; and wherein the sensor is a differential pressure sensor comprising a first and second sensing area for measuring the pressure difference between the first and second sensing areas, and wherein the pressure transfer tube is connected to the first sensing area and wherein the second transfer area is created by an orifice through the catheter body connecting the body lumen with the second sensing area, such that the sensing areas are exposed to the pressure at different locations in the body lumen, and wherein the first sensing area and the second sensing area are both within the catheter body.

2. The pressure sensor catheter according to claim 1, further comprising a second pressure transfer tube connected to the second sensing area of the sensor.

3. The pressure sensor catheter according to claim 1, wherein the pressure transfer tube is provided as a single tube having a first pressure transfer lumen and a second pressure transfer lumen.

4. The pressure sensor catheter according to claim 1, wherein the pressure transfer tube is movable and/or adjustable in length.

5. The pressure sensor catheter according to claim 1, wherein the pressure transfer tube comprises a flexible membrane.

6. The pressure sensor catheter according to claim 1, wherein the pressure transfer tube comprises a seal.

7. The pressure sensor catheter according to claim 1, further comprising a second pressure sensor in the catheter body for measuring the pressure proximal to the flow constriction.

8. The pressure sensor catheter according to claim 1, wherein the pressure transfer tube has an outer diameter smaller than the width of the sensor.

9. The pressure sensor catheter according to claim 1, wherein the pressure transfer tube comprises an opening in its side wall for passing a guidewire through a distal region of the pressure transfer tube via the distal end of the pressure transfer tube and the side wall opening.

10. The pressure sensor catheter according to claim 1, further comprising a feedthrough opening connected to the pressure transfer tube for feeding a guidewire via the feedthrough opening through at least a part of the pressure transfer tube.

11. The pressure sensor catheter according to claim 10, wherein the feedthrough opening is provided with a seal for sealing the feedthrough opening when a guidewire has been fed through.

12. The pressure sensor catheter according to claim 10, wherein the feedthrough opening is provided at distance from and proximal of the pressure sensor.

13. The pressure sensor catheter according to claim 1, wherein the pressure transfer tube is self-supporting.

14. The pressure sensor catheter according to claim 13, wherein the pressure transfer tube is formed by a tube comprising metal.

15. The pressure sensor catheter according to claim 14, wherein the pressure transfer tube and the catheter body are formed by the pressure transfer tube comprising metal, wherein a housing for housing the pressure sensor is provided to the catheter body, and wherein the housing is mechanically more stiff than the catheter body.

16. A method of positioning a pressure transfer tube for measuring a pressure on a distal side of a flow constriction in a body lumen and/or a pressure difference between a pressure on a proximal side of the flow constriction and a pressure on the distal side of the flow constriction, comprising:
   providing the pressure sensor catheter according to claim 1; and
   positioning the pressure transfer tube into the body lumen such that the sensor is located proximal of the flow constriction and is exposed to the pressure on the distal side of the flow constriction via the pressure transfer tube.

17. The method according to claim 16, wherein the step of providing a pressure sensor comprises providing a differential pressure sensor for measuring the pressure difference between a first sensing area of the sensor and a second sensing area of the sensor, wherein the pressure transfer tube is connected to the first sensing area, the method comprising positioning the pressure transfer tube such that the first sensing area is exposed to the pressure on the distal side of the flow constriction and the second sensing area is exposed to the pressure on the proximal side of the flow constriction.

18. The method according to claim 16, further comprising providing a fluid in the pressure transfer tube.

19. The method according to claim 16, wherein the pressure transfer tube comprises a feedthrough opening for feeding a guidewire via the feedthrough opening through at least a part of the pressure transfer tube, wherein the feedthrough opening is provided at a distance from and proximal of the pressure sensor, the method comprising the step of inserting the catheter over a guidewire positioned in the pressure transfer tube and the step of withdrawing the guidewire to a position in the pressure transfer tube proximal of the pressure sensor to form a pressure seal.

* * * * *